Feb. 11, 1941. F. H. HOWARD Plant Pat. 448
ROSE PLANT
Filed July 29, 1940
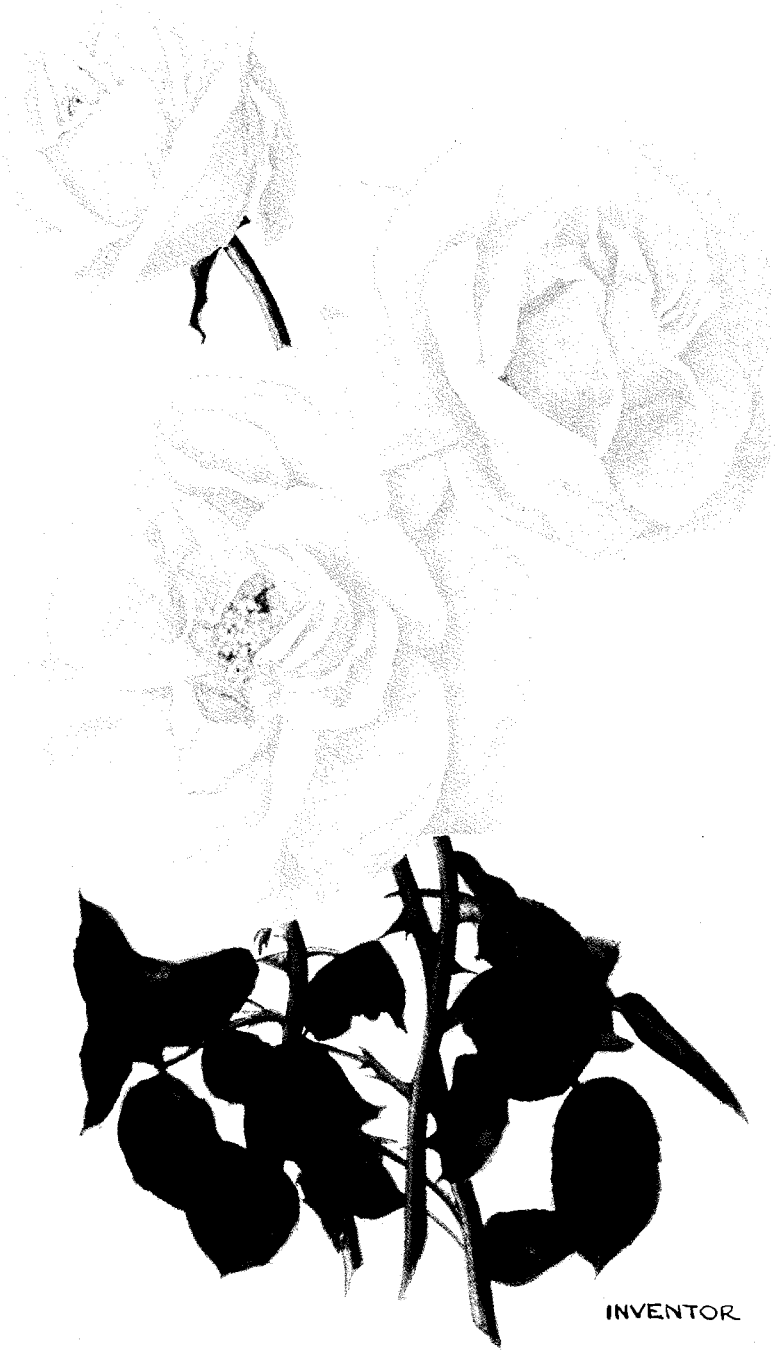
INVENTOR
Frederick Huber Howard
By Orville M. Kile
PLANT PATENT AGENT Patented Feb. 11, 1941

Plant Pat. 448

UNITED STATES PATENT OFFICE

448

ROSE PLANT

Frederick Huber Howard, Montebello, Calif.

Application July 29, 1940, Serial No. 348,270

1 Claim. (Cl. 47—61)

My new invention pertains to improvements in climbing hybrid tea roses and is the result of a cross of Ednah Thomas by Autumn, made by me in my gardens.

This is an unusually vigorous climbing rose variety and the leathery foliage is mildew-proof, thus making an excellent rose for screening purposes.

It has been asexually reproduced and its outstanding qualities have proved to be permanent.

The original illustrations accompanying this application depict in approximately their true form and colors, three specimens of this variety in different stages of maturity.

Following is a detailed description of the plant and flower, reference being made to Ridgway's Color Standards and Nomenclature except where the ordinary dictionary meaning is obviously intended.

*The plant*

Growth: Very vigorous climber, attaining a height of from 12 to 18 feet.

Blooming habit: Profuse bloomer all season.

Disease resistance: Very resistant to common rose diseases, particularly mildew which has never been found on this variety.

Foliage: Abundant; compound, usually 3 to 5 leaflets.

*Leaflets.*—*Size*—small, terminal leaflet 1¾ to 2 inches in length by 1¼ to 1½ inches in width. Lateral leaflets smaller. *Shape*—ovate with acute tip and rounded base. *Margin*—entire. *Texture*—leathery. *Color*—approximately Cedar Green (Plate VI) on the upper surface; lower surface—Light Elm Green (Plate XVII). *Appearance*—glossy; clean.

Rachis: Thin; grooved above; occasional small thorns below.

Stipules: Long; narrow; clinging; narrow acute points extend at broad angle.

Stems: Long; strong; inclined to be staggered from node to node.

*Color.*—Cerro Green (Plate V) to Olive Green (Plate IV), frequently overlaid with bronze or reddish tinge.

Thorns: Downward-hooked; sharp; approximately Van Dyke Red (Plate XIII); irregularly placed on stem; progressively larger and more frequent downward on the stem.

*The flower*

Bud:

*Size.*—Large.

*Shape.*—Long-pointed; opens urn-shaped.

*Color.*—From Eugenia Red (Plate XIII) at the base to Strawberry Pink (Plate I) at the tip.

*Peduncle.*—Short to medium; stiff; straight; covered with very fine spines; its Olive Green color is usually heavily tinged with Neutral Red (Plate XXXVIII).

*Sepals.*—Simple; medium length; turn backward, clasping peduncle.

Blossom:

*Borne.*—Singly on peduncles which are short to medium.

*Size.*—Very large for climbing rose, often reaching 5 inches in diameter.

*Form.*—Cupped, becoming loose as it opens. Petals much folded and imbricated.

*Petalage.*—Double, with 20 to 30 petals.

*Color.*—General color effect is that of a bi-color rose, one color being in the buff shades and the other in the red to orange shades.

Petals:

*Shape.*—Outer petals approximately round and slightly cupped. Inner petals narrower and more deeply cupped. *Edge*—usually smooth except for occasional irregular notches at tip. Edges roll back slightly as flower ages.

*Texture.*—Thick.

*Appearance.*—Dull.

*Size.*—Large; outer petals approximately 2½ by 2½ inches.

*Color.*—As the bud opens it becomes lighter in color and the bi-color effect becomes evident. The inner surface of the petals of the opened flower is Buff Yellow (Plate IV) with a suffusion of Vinaceous-Pink (Plate XXVIII). The outer surface contains a range of colors from Jasper Pink (Plate XIII), through Light Jasper Red (Plate XIII) and Old Rose (Plate XIII), with occasional touches of Spinel Pink (Plate XXVI). The base of all the petals is Light Cadmium (Plate IV), which is evident in larger quantity on the inner surface. The inner petals frequently remain folded in such a way as to display the color of the outer surface in contrast with the color of the inner surface.

Longevity: Very good.
Fragrance: Slight.
Behavior: Petals drop off cleanly.
Reproductive organs:

*Pistils.*—Many; bunched. *Styles*—short; light yellow. *Stigmas* — approximately Spinel Red (Plate XXVI), tipped with Naples Yellow (Plate XVI).

*Stamens.*—Many; arranged around bunched pistils. *Filaments*—irregular in length, extending beyond pistils; Empire Yellow (Plate IV). *Anthers*—large; approximately Light Cadmium (Plate IV).

*Ovaries.*—Large; ovoidal; smooth; inclosed.

Having thus disclosed my invention, I claim:

A new and distinct variety of climbing hybrid tea rose plant, characterized particularly by its continuous and free blooming habit; its healthy, mildew-resistant foliage; and its large, well-formed, double flowers of a distinctive color for climbing roses, having a bi-color effect composed of tints and shades from Buff-Yellow to Eugenia Red, substantially as shown and described.

FREDERICK HUBER HOWARD.